(12) United States Patent
Aldstadt, III et al.

(10) Patent No.: US 9,013,700 B2
(45) Date of Patent: Apr. 21, 2015

(54) VARIABLE PATH LENGTH PHOTON TRAPPING SPECTROMETER

(75) Inventors: Joseph Aldstadt, III, West Bend, WI (US); Peter Geissinger, Shorewood, WI (US); Beth A. Ruddy, West Allis, WI (US); Jörg C. Woehl, Bayside, WI (US); John A. Frost, Harshaw, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 536 days.

(21) Appl. No.: 13/401,718

(22) Filed: Feb. 21, 2012

(65) Prior Publication Data

US 2012/0212739 A1  Aug. 23, 2012

Related U.S. Application Data

(60) Provisional application No. 61/444,953, filed on Feb. 21, 2011.

(51) Int. Cl.
*G01N 21/00* (2006.01)
*G01J 3/02* (2006.01)
*G01J 3/04* (2006.01)
*G01J 3/10* (2006.01)
*G01J 3/32* (2006.01)

(Continued)

(52) U.S. Cl.
CPC .............. *G01J 3/0291* (2013.01); *G01J 3/0205* (2013.01); *G01J 3/021* (2013.01); *G01J 3/04* (2013.01); *G01J 3/10* (2013.01); *G01J 3/32* (2013.01); *G01J 3/42* (2013.01); *G01N 21/552* (2013.01); *G01J 3/0229* (2013.01); *G01J 3/0232* (2013.01); *G01N 21/3504* (2013.01); *G01N 21/0303* (2013.01); *G01N 21/031* (2013.01); *G01N 21/31* (2013.01); *G01N 2021/317* (2013.01)

(58) Field of Classification Search
CPC ...................................................... G01N 21/031
USPC ........................................... 356/436, 312, 454
See application file for complete search history.

(56) References Cited

U.S. PATENT DOCUMENTS 3,857,641 A * 12/1974 Gass .............................. 356/438
3,885,162 A *  5/1975 Geertz ........................... 356/439
2007/0242720 A1* 10/2007 Eckles et al. ................... 372/107

OTHER PUBLICATIONS

Bechtel, K.L., et al., "Moving beyond traditional UV-visible absorption detection: Cavity ring-down spectroscopy for HPLC", (2005) Analytical Chem. 77: 1177-1182.

(Continued)

*Primary Examiner* — Kara E Geisel
(74) *Attorney, Agent, or Firm* — Michael Best & Friedrich LLP

(57) ABSTRACT

A system and method of photon trapping spectroscopy to vary the path length of light for use in spectroscopy. The systems and method include a rotating reflector with slits for selectively permitting light to enter and exit into a reflection cavity containing a sample to be analyzed. After entering the cavity, but before exiting, the light is trapped and repeatedly reflects back and forth through a sample, effectively increasing the path length of light through a sample. The effective path length is quickly adjustable by altering the rotation speed of the rotating reflector to alter the time in which the light is trapped within the cavity. The systems and methods provide a spectroscope with a wide dynamic range, low detection limits, and usable with broadband and monochromatic light sources throughout the optical region (ultraviolet to infrared).

12 Claims, 13 Drawing Sheets

(51) Int. Cl.
G01J 3/42 (2006.01)
G01N 21/3504 (2014.01)
G01N 21/03 (2006.01)
G01N 21/31 (2006.01)
G01N 21/552 (2014.01)

(56) References Cited

OTHER PUBLICATIONS

Chernin, S.M. "Multipass system with large relative aperture", (1992) Journal of Modern Optics. 39(3): 525-532.
Dasgupta, P.K., et al., "Multi-path cells for extending dynamic range of optical absorbance measurements", (1984) Analytical Chemistry. 56: 1401-1403.
Frost, J.A. et al. "Photon Trapping Spectroscopy: Theory and development", Oct. 18-22, 2009, Louisville, Kentucky, Federation of Analytical Chemistry and Spectroscopy Societies.
Herriot, D.R., et al., "Folded optical delay lines", (1965) Applied Optics. 4: 883-889.
Mazurenka, M., et al., "Evanescent cavity ring-down spectroscopy in a thin-layer electrochemical cell", (2006) Analytical Chem. 78: 6833-6839.
Moring, S.E., et al., "Optical improvements of a Z-shaped cell for high sensitivity UV absorbance detection in capillary electrophoresis", (1993) Analytical Chem. 65: 3454-3459.
O'Keefe, A., et al., "Cavity ring-down optical spectrometer for absorption-measurements using pulsed laser sources," (1988) Review of Scientific Instruments. 59: 2544-2551.
Paldus, B.A., and Zare, R.N. "Absorption spectroscopies: From early beginnings to cavity-ring-down spectroscopy", (1999). Cavity-Ringdown Spectroscopy: An ultra-trace absorption measurement technique. K.W. Busch, M.A. Busch, Editors, ACS Symposium Series (No. 720). Washington, D.C.
Pipino, A.C.R., et al., "Evanescent wave cavity ring-down spectroscopy with a total-internal-reflection minicavity", (1997) Rev. of Scientific Instrum. 68: 2978-2989.
Scherer, J.J., et al., "Cavity ring-down laser absorption spectroscopy: History, development, and application to pulsed molecular beams", (1997) Chemical Reviews. 97: 25-52.
Snyder, K., et al., "Cavity ring-down spectroscopy as a detector for liquid chromatography", (2003) Analyt. Chem. 75: 3086-3091.
Van Der Sneppen, L., et al., "Cavity ring-down spectroscopy for detection in liquid chromatography and UV wavelengths using standard cuvettes in a normal incidence geometry", (2007) Journal of Chromatography. 1148: 184-188.
Van Der Sneppen, L., et al., "Liquid-phase and evanescent-wave cavity ring-down spectroscopy in analytical chemistry", (2009) Ann. Rev. Analytic. Chem. 2: 13-35.
White, J.U. "Long optical paths of large aperture", (1942) Journal of the Optical Society of America. 32: 285-288.

* cited by examiner

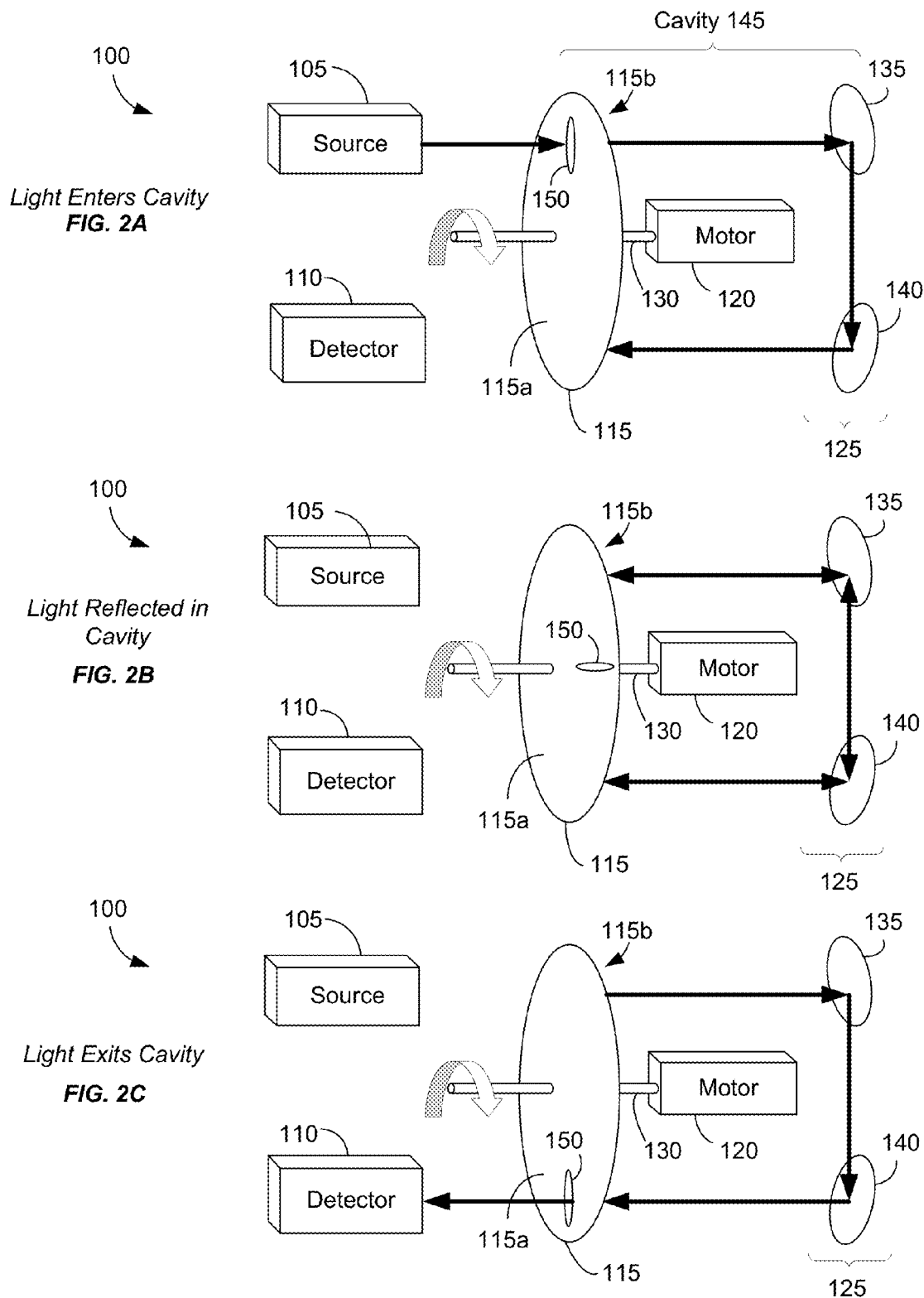

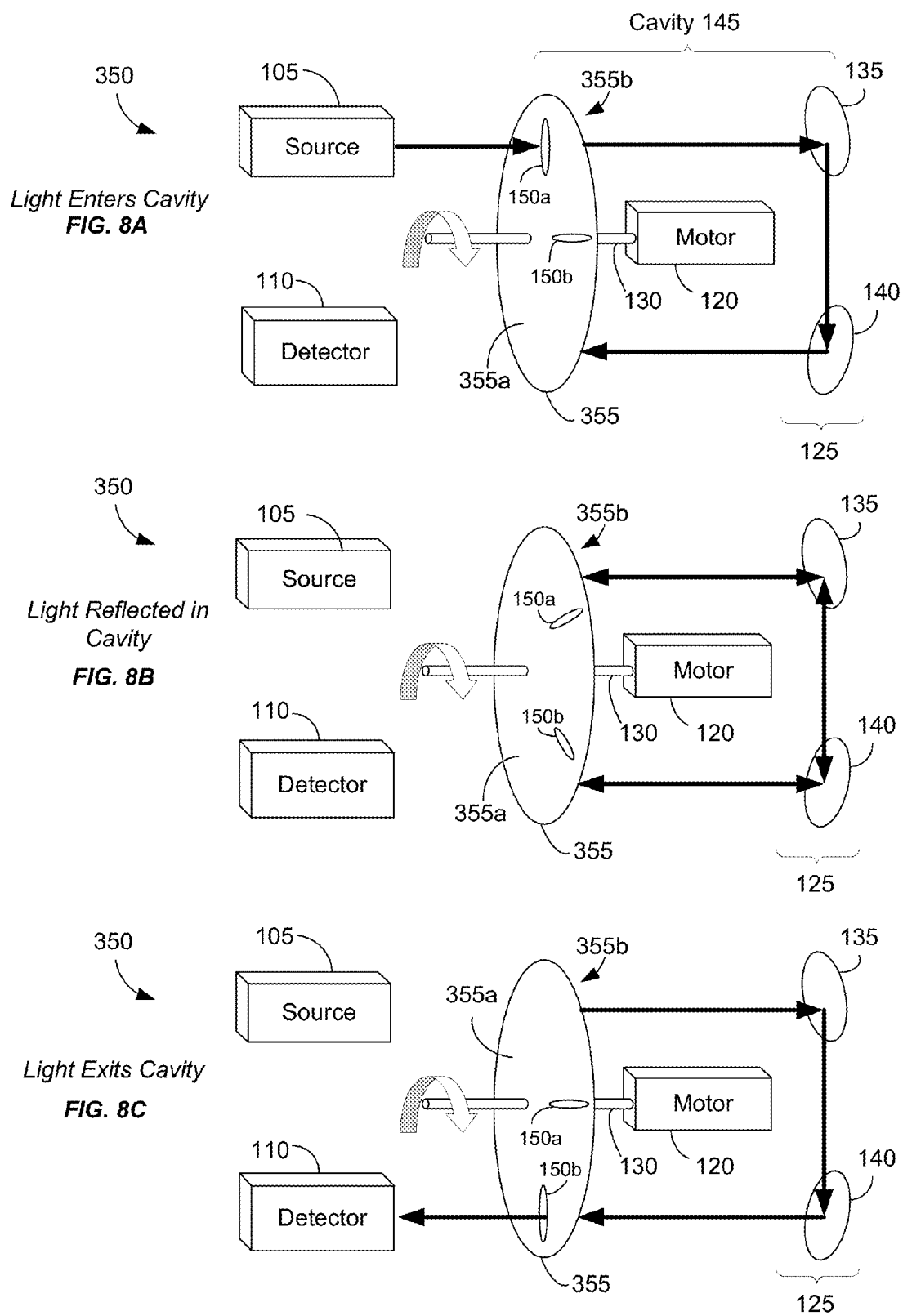

Light Enters Cavity

Light Reflected in Cavity

Light Exits Cavity

VARIABLE PATH LENGTH PHOTON TRAPPING SPECTROMETER

BACKGROUND

Embodiments of the present invention relates to spectroscopy.

SUMMARY

In general, spectroscopy is the study of the interaction of electromagnetic radiation (EMR) with matter to probe the chemical and/or physical properties of atoms and molecules. For example, the absorption of EMR by a chemical species can be used to quantitatively determine the chemical concentration of that species in a sample. Consider a spectroscopic experiment 50 based on the absorption of visible light by an aqueous solution, schematically shown in FIG. 1. In FIG. 1, a light source 55 emits EMR towards a light detector 60. An optical cell compartment 65 containing the aqueous sample solution is positioned between the light source 55 and light detector 60. If the aqueous sample solution contains a molecule (X-Y) that can absorb EMR at a particular wavelength, a fraction of the incident light power will be absorbed by the solution and not transmitted to the detector 60. The transmittance—the ratio of the transmitted light power (P) to the incident light power ($P_0$)—will decrease as the absorbance increases. Ideally, the amount of light that is absorbed by X-Y is directly proportional to the concentration of X-Y in the sample, as described by the Beer-Lambert-Bougher Law ("Beer's Law"):

$$A = \in bC$$

where A is the absorbance—the negative of the base-10 logarithm of the transmittance (unitless); $\in$ is the molar absorptivity of X-Y, which is a probabilistic function of chemical structure (liters per mole-cm); b is the path length of light—the distance the light travels through the sample compartment (cm); and C is the concentration of X-Y in the sample (moles per liter). Other interactions of EMR with matter, e.g., the emission and scattering of light, may also be measured in spectroscopy, although they use different theoretical relationships between the EMR and emission or scattering phenomena.

When applying Beer's Law, such as in experiment 50, A is directly proportional to b—the only experimental variable, $\in$ is a constant for a given chemical structure, A is measured by the light detector 65, and C is calculated based on the values of A, $\in$, and b. In practice, however, b is limited to relatively small values, such as 1.0 cm, and cannot be simply increased to measure lower concentrations of a molecule such as X-Y.

Embodiments of the present invention provide a system and method to vary the path length (b) of light in spectroscopy, enabling the analysis of molecules having a low concentration (c) or low molar absorptivity value ($\in$) that otherwise would have an absorbance level (A) that is too small to detect (e.g., due to noise).

In one embodiment, the invention provides a variable path length photon trapping spectrometer. The spectrometer includes a rotating reflector, a light source, a cavity, a reflector arrangement, and a light detector. The rotating reflector has a source side, a cavity side, and a slit providing a passage between the source side and the cavity side. The light source emits light towards the rotating reflector and through the slit as the rotating reflector rotates. The cavity receives the light that passes though the slit. The reflector arrangement is positioned opposite the cavity side of the rotating reflector and reflects the light received by the cavity back towards the cavity side of the rotating reflector. The light detector is positioned opposite the source side of the rotating reflector to receive the light reflected by the reflector arrangement, which has exited the cavity through one of the slit and a second slit of the rotating reflector.

In another embodiment the invention provides a method of variable path length photon trapping spectrometry. The method includes rotating a rotating reflector having a source side, a cavity side, and a slit providing a passage between the source side and the cavity side. A light source emits light through the slit, which is received by a cavity formed between a reflector arrangement and the rotating reflector. The light is reflected by the reflector arrangement back towards the cavity side of the rotating reflector. A light detector positioned opposite the source side of the rotating reflector receives the light reflected by the reflector arrangement, which has exited the cavity through one of the slit and a second slit of the rotating reflector.

Other aspects of the invention will become apparent by consideration of the detailed description and accompanying drawings.

BRIEF DESCRIPTION OF THE DRAWINGS

FIGS. 2A-C illustrate a variable path length spectrometer system.

FIGS. 8A-C illustrate another variable path length spectrometer system.

DETAILED DESCRIPTION

Figure 1:
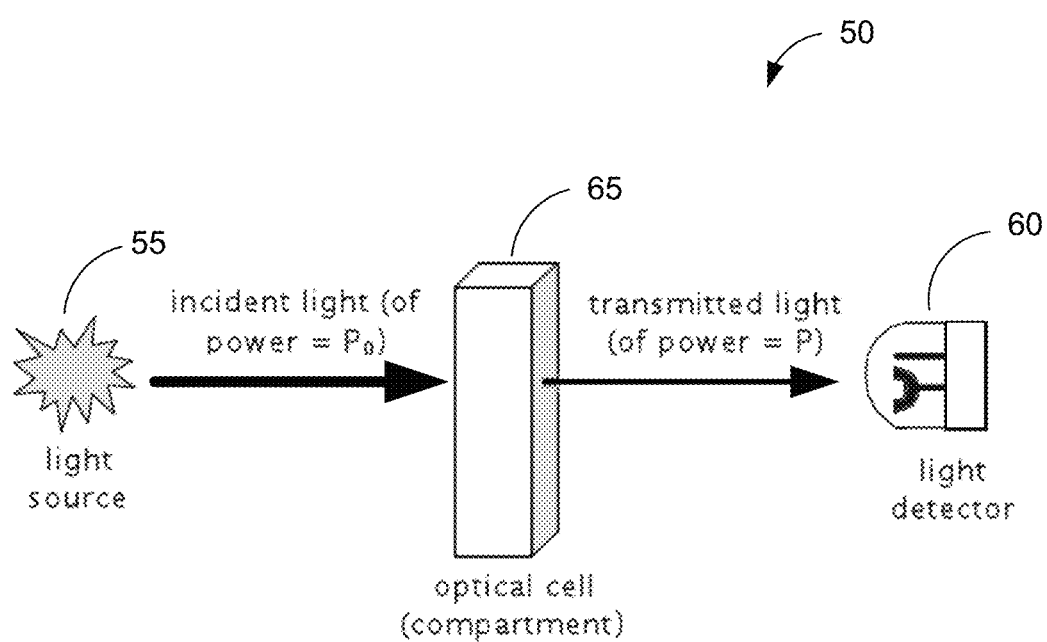
FIG. 1 illustrates a spectroscopic experiment based on the absorption of visible light by an aqueous solution.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

FIGS. 2A-C illustrate a variable path length spectrometer system 100. The system 100 includes a light source 105, a detector 110, a rotating reflector 115 rotated by a motor 120, and a reflecting arrangement 125. The light source 105 may be controlled to selectively emit light of a selected wavelength in the ultraviolet, visual, or infrared spectrum (i.e., the optical region) or to other regions of the electromagnetic spectrum given suitable optical components. The light may be emitted as a polarized, collimated beam, or may be collimated and polarized post-emission. The light may be discrete (monochromatic) or continuous (polychromatic), or may be continuous wave or pulsed.

The detector 110 receives light and, in response, outputs electric signals representing characteristics of the light received. The detector 110 may be single-channel (e.g., a photomultiplier tube) or multi-channel (e.g., a charge-transfer device). The rotating reflector 115 is coupled to the motor 120 via axle 130. The motor 120 rotates the axle 130, which causes the rotating reflector 115 to rotate. The reflecting arrangement 125 includes a reflector 135 and a reflector 140. The reflectors 135 and 140 may be implemented as concave, fixed mirrors that precisely direct the light, and may also be referred to as folding mirrors. In some instances, the reflectors 135 and 140 include aligning actuators to accurately position the reflector 135 and 140 for proper reflection of light between the rotating reflector and each other. Nonetheless, with the exception of alignment, the reflectors 135 and 140 may are fixed (i.e., not rotating) during a photon-trapping instance. The area between the rotating reflector and the reflecting arrangement 125 forms a cavity 145 for photon trapping.

The rotating reflector 115 further includes a source side 115a and a cavity side 115b (not in view in FIGS. 2A-C). The rotating reflector 115 has a slit 150 providing a passage between the source side 115a and the cavity side 115b. The cavity side 115b is a substantially flat mirror (ideally, perfectly flat). Generally, the slit 150 has flat, smooth edges perpendicular to the flat mirror surface (the cavity side 115b) to prevent scattering of light passing through the slit 150.

In some embodiments, the slit 150 may be precisely machined into the cavity side 115b using, for instance, a computer numerical control (CNC) machine. In some embodiments, a rotating reflector 115 without a slit 150 is used as a starting point. A focused ion beam (FIB) is then used to remove an approximately 1 μm thick dielectric layer in the shape of the slit 150. FIB milling includes an intense beam of gallium ions that precisely remove the dielectric material until the desired slit geometry is obtained using, for instance, a Zeiss 1500XB Cross Beam™ system having a milling precision of 7 nm with a 30 kV FIB source. In another alternate manufacturing process, the rotating reflector 115 may be produced by repeatedly depositing layers of dielectric (reflective) material on a base (mirror blank), and using a mask-shadow deposit technique to prevent reflective material from being deposited in an area having the shape of the slit 150.

Returning to FIGS. 2A-C, three stages of operation of the system 100 are illustrated. In FIG. 2A, the light source 105 emits light towards the rotating reflector 115. As the rotating reflector 115 rotates, the slit 150 becomes aligned with the emitted light of the source 105. The emitted light passes through the slit 150 and enters the cavity 145. The light is then reflected by reflector 135 towards reflector 140, which reflects the light back to the cavity side 115b of the rotating reflector 115.

As shown in FIG. 2B, the rotating reflector 115 continues to rotate and the slit 150 is no longer aligned with the light source 105. Accordingly, further light is prevented from entering the cavity 145. The light that previously entered into the cavity 145, however, is trapped. The trapped light will continue to reflect within the cavity 145 between the cavity side 115b of the rotating reflector 115 and the reflecting arrangement 125.

In FIG. 2C, the slit 150 becomes aligned with the detector 110 and the light trapped in the cavity 145 exits through the slit 150 towards the detector 110. While the light is trapped in the cavity 145 (FIG. 2B), the light is repeatedly reflected within the cavity 145, which increases the path length of the light. By varying the rotation speed of the rotating reflector 115, the duration between the slit 150 moving from the light entering position (FIG. 2A) to the light exiting position (FIG. 2C) is varied. The number of reflections between the rotating reflector 115 and the reflecting arrangement 125 is proportional to this variable duration. Accordingly, the path length of the light from source 105 to detector 110 is adjusted by adjusting the rotation speed of the rotating reflector 115. In some embodiments, the rotation speed of the rotating reflector 115 is between 10,000 and 15,000 RPM, although other rotation speeds may also be used.

Although the light source 105 is shown as not emitting light in FIGS. 2B-C, the source 105 may continue to emit light in these stages, but it will not pass into the cavity 145 as the slit 150 will be out of alignment with the light source 105. Additionally, pulsing of the source light 105 when the slit 150 is aligned may be used to reduce scattering effects that are encountered when the light beam passes along the edges of the slit 150. That is, when the slit 150 becomes aligned as the rotating reflector 115 rotates, the source light 105 briefly emits light, and then ceases emitting light before the rotating reflector 115 rotates such that the light reaches the edge of the slit 150.

The rotating reflector 115 and reflectors 135 and 140 are mirrors having approximately 99.9% reflectivity or higher. The high reflectivity limits the amount of light lost during each reflection to approximately 0.1%. Thus, for a 99.9% reflective mirror, after 1000 reflections all of the light is lost to the mirrors.

Figure 3A:
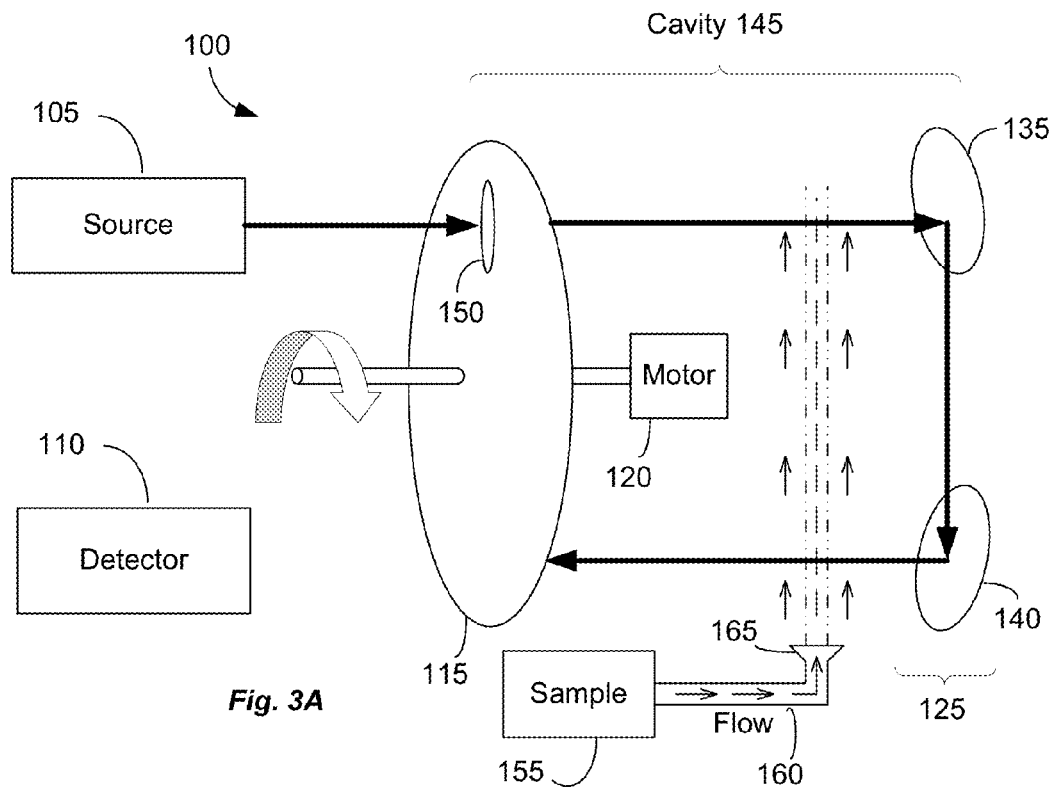
FIGS. 3A-B illustrate techniques for exposing a sample to reflecting light within a cavity.
Figure 3B:
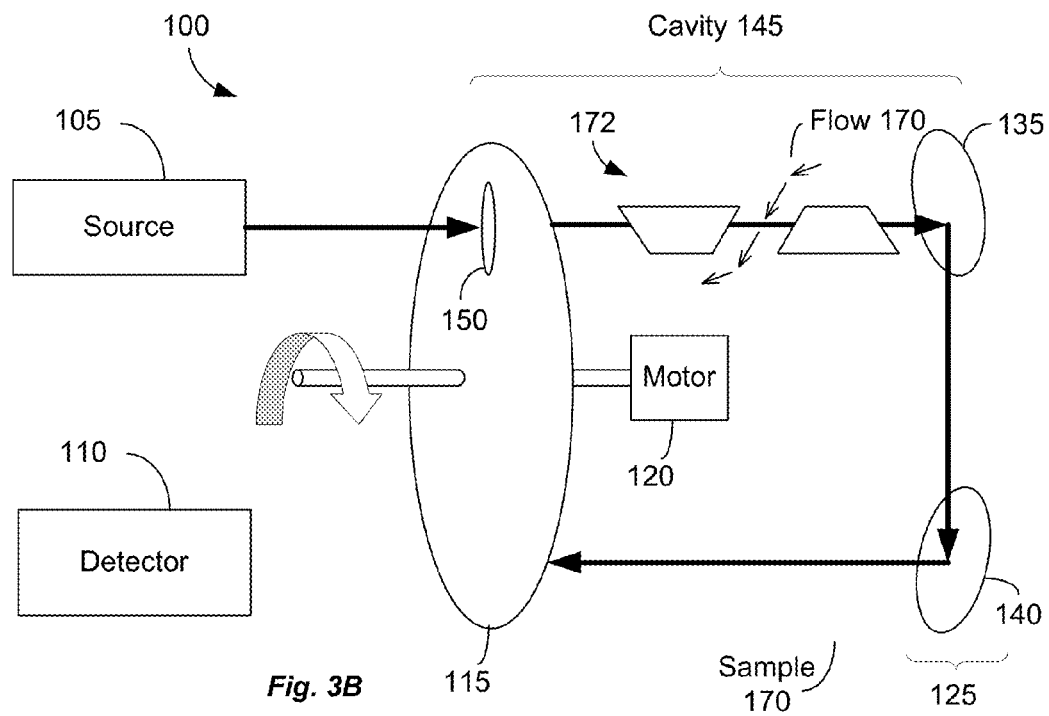

FIGS. 3A-B illustrate two techniques for exposing a sample to the reflecting light within the cavity 145. In FIG. 3A, a sample 155 in gas form is directed across the cavity 145. The sample 155 is directed through a flow tube 160 and emitted by a nozzle 165. The sample 155 then flows across the cavity 145 such that the reflecting light passes through the sample 155. The flow of the sample 155 may be located in various positions within the cavity 145. In some instances, the flow of the sample 155 is directed between either the reflector 135 and the rotating reflector 115, or the reflector 140 and the rotating reflector 115. In some instances, the flow of the sample 155 is directed between the reflector 140 and the rotating reflector 135.

Figure 4A:
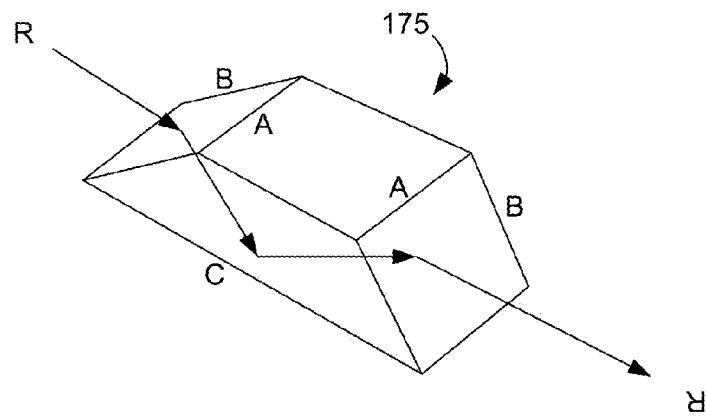
FIGS. 4A-C illustrate techniques using Dove prisms for liquid films and flow-through cells.
Figure 4B:
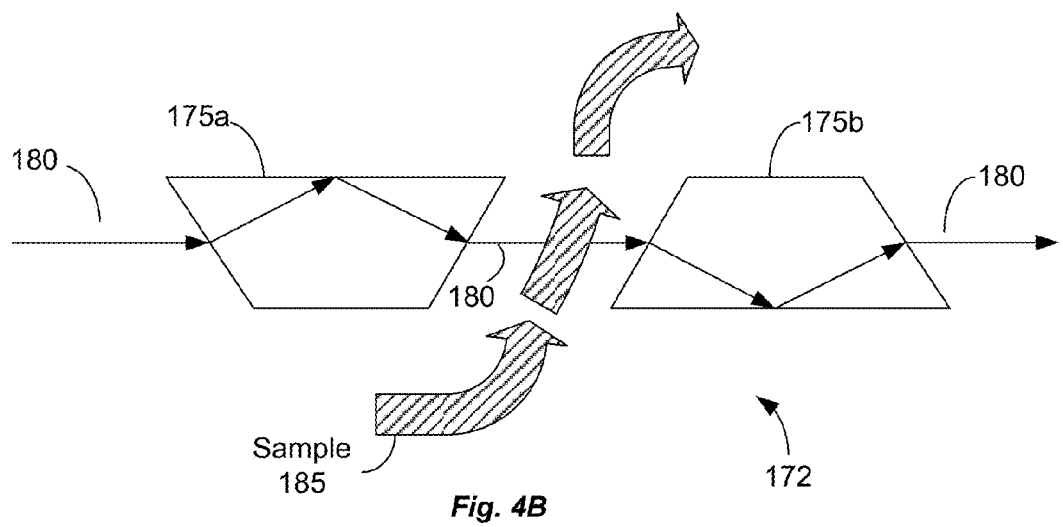
Figure 4C:
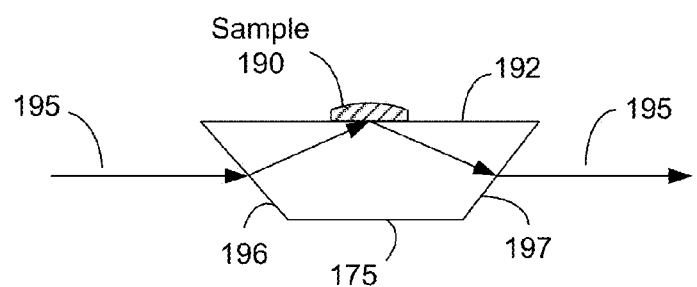

In FIG. 3B, a liquid or gas sample flow 170 is directed within the cavity 145 via a Dove prism arrangement 172, which is explained in further detail with respect to FIGS. 4A-C. Accordingly, light passes through the solution during every reflection between the rotating reflector 115 and the reflector 135. The flow 170 may be directed in various positions within the cavity 145. In some instances, the Dove prism arrangement 172 is positioned such that the flow 170 is directed between the reflector 140 and the rotating reflector 115, or between the reflector 140 and the reflector 135.

When light passes through an air:glass or glass:water interface, the light is refracted (bent). If not addressed, this effect can quickly bend the light off of the desired optical axis. For this reason, and for avoiding reflection losses inherent in an air:glass interface, a conventional sample cuvette or glass slide to contain liquid or support solid samples generally cannot be inserted into the beam path without creating sub-cavities that may negatively impact quantitative measurements with the spectrometer. As shown in FIG. 4A, a Dove prism 175 may be used to direct the beam of light along a desired optical axis. In the Dove prism 175, light R entering face AB is internally reflected in such a way that the light R emerges parallel (and inverted) to the original beam axis. As shown in FIG. 4B, Dove prisms 175a and 175b are used to direct the flow (e.g., the flow 170 of FIG. 3B) to enable the light to remain on the desired optical axis 180 while passing through the flow 170. The FIG. 4B arrangement may be referred to as a "paired cell" design.

In FIG. 4C, a technique based on evanescent waves is used, which may be referred to as an "evanescent wave cell" design. In essence, a sample 190 is deposited on a top face 192 of the Dove prism 175 (e.g., as a drop of liquid or as a polymeric film) such that the sample is perpendicular to a beam axis 195. The prism 175 is cut such that light striking an entrance face 196 at Brewster's angle ($\alpha_P$, where $\tan(\alpha_P)=n_{prism}/n_{air}$), if polarized in the plane of incidence, enters the Dove prism 175 without light being reflected off of the entrance face 196, allowing the beam to enter the prism 175 without losses. Upon passing through the entrance face 196, the beam is refracted towards the top face 192. The beam then reflects off of the top surface 192 towards an exit face 197 such that the beam incident on the entrance face 196 and the beam refracted out of the prim 175 through the exit face 197 are co-linear. When the beam meets the top surface 192, the evanescent wave portion of the beam is absorbed by the sample. The absorption may be analyzed using similar techniques and calculations as described above with light passing through a sample (e.g., as shown in FIG. 4B). In some embodiments, the sample 190 is a flowing liquid in a channel. For instance, the Dove prism 175 may form the bottom of the channel, and the sample 190 flows through the channel along the top of the Dove prism 175. Other techniques of providing a sample in the path of the reflecting light of the cavity 145 are also possible.

As noted above, by varying the rotation speed of the rotating reflector 115, the path length of the light from source 105 to detector 110, and through a sample to be analyzed, is adjusted. Accordingly, the system 100 enables a wide range of, and significant increases to, the path length b of Beer's Law ($A=\in bC$). In turn, the system 100 is able to analyze samples with a low concentration (C) or low molar absorptivity value ($\in$) that otherwise would have an absorbance level (A) that is too small to detect (e.g., due to noise).

Figure 5A:
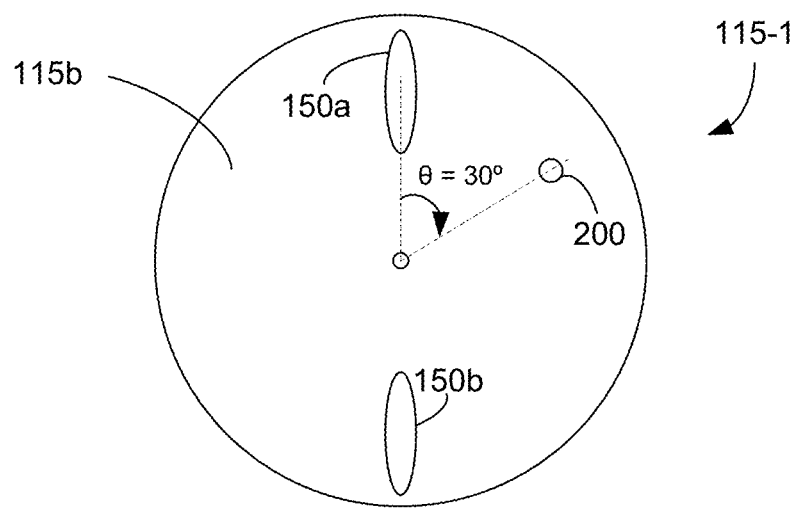
FIGS. 5A-B illustrate rotating reflectors with various slit arrangements.

Several equations, described below, are used to calculate the effective path length (b*) of the light through the sample for use in Beer's Law. The time for the rotating reflector 115 to make one revolution is given by the equation $t_{rot}=f^{-1}$, where f is the rotational frequency of the mirror in Hertz (Hz). With reference to FIG. 5A, the amount of time that the light stays trapped inside the cavity 145 is equal to the time that the rotating reflector 115 takes to rotate angle $\theta$. The angle $\theta$ is formed between the center of the projected beam spot 200 on the rotating reflector 115 and the slit 150a, which serves both as the "entrance" and "exit" slit in FIG. 5A. The amount of time that the light stays trapped inside the cavity 145 ($t_{cav}$) is: $t_{cav}=t_{rot}(\theta/360)$, where $\theta$ is measured in degrees. The distance traveled by the light during this time ($d_T$) is: $d_T=c_a t_{cav}$, where $c_a$ is the speed of light in air ($2.997 \times 10^8$ m s$^{-1}$). The total number of reflections ($N_r$) that occur during this time is $N_r=n_r(d_T/d_r)$, where $d_p$ is the cavity path length (the distance from the cavity side 115b of the rotating reflector 115 to the reflectors 135 and 140 and back) and $n_r$ is the number of reflections when traveling $d_p$. Note that the percentage of light power transmitted (P) after N reflections from a mirrored surface of specific reflectivity (R) is given by: $P=R^{Nr}$. P may be greater than 0.05% for convenient measurements. The total number of passes through a sample placed in the beam path is given by: $N_s=d_T/d_p$. Thus, the effective sample path length (b*) is: $b^*=b \times N_s$. The amplification factor achieved (AF) is $AF=b^*/b$. Substitution of the factors derived above yields a theoretical expression for b*: $b^*=(b c_a \theta)/(360 d_p f)$. If the frequency of rotation is expressed in rotations per minute (rpm) the expression for b* is: $b^*=(b c_a \theta)/(6 d_p f)$.

Exemplary Beer's Law calculations for the variable path length spectrometer are provided below. The example assumes that the rotating reflector 115 and reflectors 135 and 140 are flat, that the light is a beam that remains collimated, that the motor does not induce wobble of the rotating reflector 115, and that the speed of light in air ($c_A$) is $2.997 \times 10^8$ m s$^{-1}$. In the example, the rotating reflector 115 rotates at 90 Hz, a frequency that is attainable using commercial high-speed rotary motors. The width of the sample compartment is 0.10 mm, and the cavity is 3.0 m. The time that the light is trapped within the cavity (i.e., passing through the sample) is about 11 ms. In this period of time, the trapped photons will travel almost 300 km, the light will be reflected almost 300,000 times, and approximately 6% of the source light will still be present for detection. The resulting path length thus increases from 0.10 mm to 9.25 m-almost a 100,000-fold improvement.

| Variables | Description | Value |
| --- | --- | --- |
| b | path length prior to amplification | 0.10 mm |
| R | mirror reflectivity (of rotating reflector 115 and reflectors 135 and 140) | 99.999% |
| f | frequency of rotation | 90 Hz (5,400 RPM) |
| $d_p$ | distance within cavity | 3.0 m |
| $\theta$ | angular offset | 30° |

| Calculated Parameters | Description | Value |
| --- | --- | --- |
| $t_{rot}$ | time to rotate rotating reflector once | $1.11 \times 10^{-2}$ (s) |
| $t_{cav}$ | time light remains trapped | $9.26 \times 10^{-4}$ (s) |
| $d_T$ | total distance traveled by light | 277,500 (m) |
| $N_r$ | number of reflections | 277,500 |
| P | fraction of intensity transmitted | 6.23% |
| $N_s$ | number of passes through the sample | 92,500 |
| b* | effective sample path length | 9.25 (m) |
| AF | amplification factor | 92,500 |

Figure 5B:
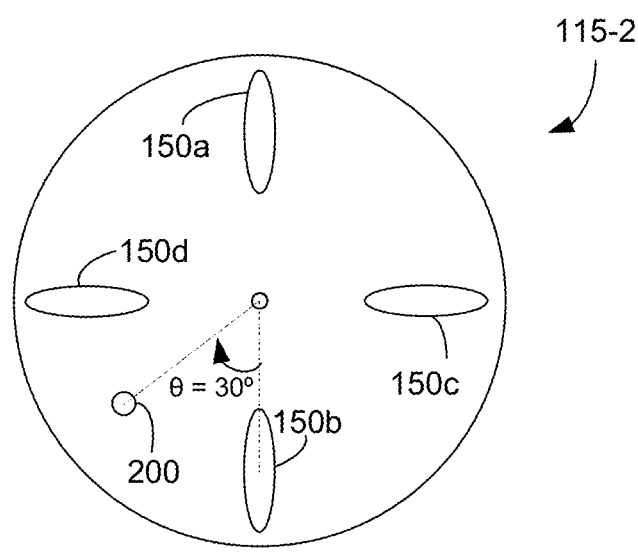

Additional slits may be provided on the rotating reflector 115 for balance and/or for increasing the duty cycle of the system. FIGS. 5A-B each illustrate a rotating reflector 115 with more than one slit 150—FIG. 5A depicting a rotating reflector 115-1 and FIG. 5B depicting a rotating reflector 115-2. The rotating reflector 115-1 includes two slits: 150a and 150b. Light enters into the cavity 145 via the slit 150a and is reflected by the reflecting arrangement 125 back to the cavity side at a projected beam spot 200. Accordingly, upon rotation of 30 degrees ($\theta$), the slit 150a becomes aligned with the projected beam spot 200, and the trapped light exits the cavity 145. In FIG. 5B, the rotating reflector 115-2 includes four slits: 150a-d. Light enters into the cavity 145 via the (entrance) slit 150a and is reflected by the reflecting arrangement 125 back to the cavity side at a projected beam spot 200. Accordingly, upon rotation of 30 degrees ($\theta$), the (exit) slit 150b becomes aligned with the projected beam spot 200, and the trapped light exits the cavity 145. In some embodiments, other slit arrangements for the rotating reflector 115 beyond what is shown in FIGS. 5A-B are used.

By projecting the projected beam spot 200 and/or adding/removing slits 150 to various locations on the rotating reflector 115, the angle of rotation ($\theta$) can be varied, and the time that light is in the cavity ($t_{cav}=t_{rot}(\theta/360)$) can be altered without changing the rotation speed of the motor 120. These variables, along with altering rotation speed of the rotating reflector 115, enable a wide range of potential effective path lengths (b*).

The high speed rotation of the motor 120 may result in a wobble of the rotating reflector 115. The wobble can cause a deviation of the cavity light from the desired optical path. Evenly distributing the weight of the rotating reflector 115 relative to the axis of rotation can minimize wobble of the rotating reflector 115. Introducing the slit 150a, without the slit 150b on the opposite side (see, e.g., FIG. 3A, in contrast to FIG. 5A), may create an uneven distribution of weight of the rotating reflector 115. Accordingly, in some embodiments, slit pairs are positioned directly across (180 degrees) from each other to balance the weight of the rotating reflector 115. See, for instance, FIG. 5B, where the slits 150a and 150c in FIG. 5B are balanced by the slits 150b and 150d, respectively. In some embodiments, rather than balancing the rotating reflector 115 by adding a slit-pair, other weight balancing techniques are implemented. For instance, counter weights are added to or weight is removed (without slits) from the rotating reflector 115.

Figure 6:
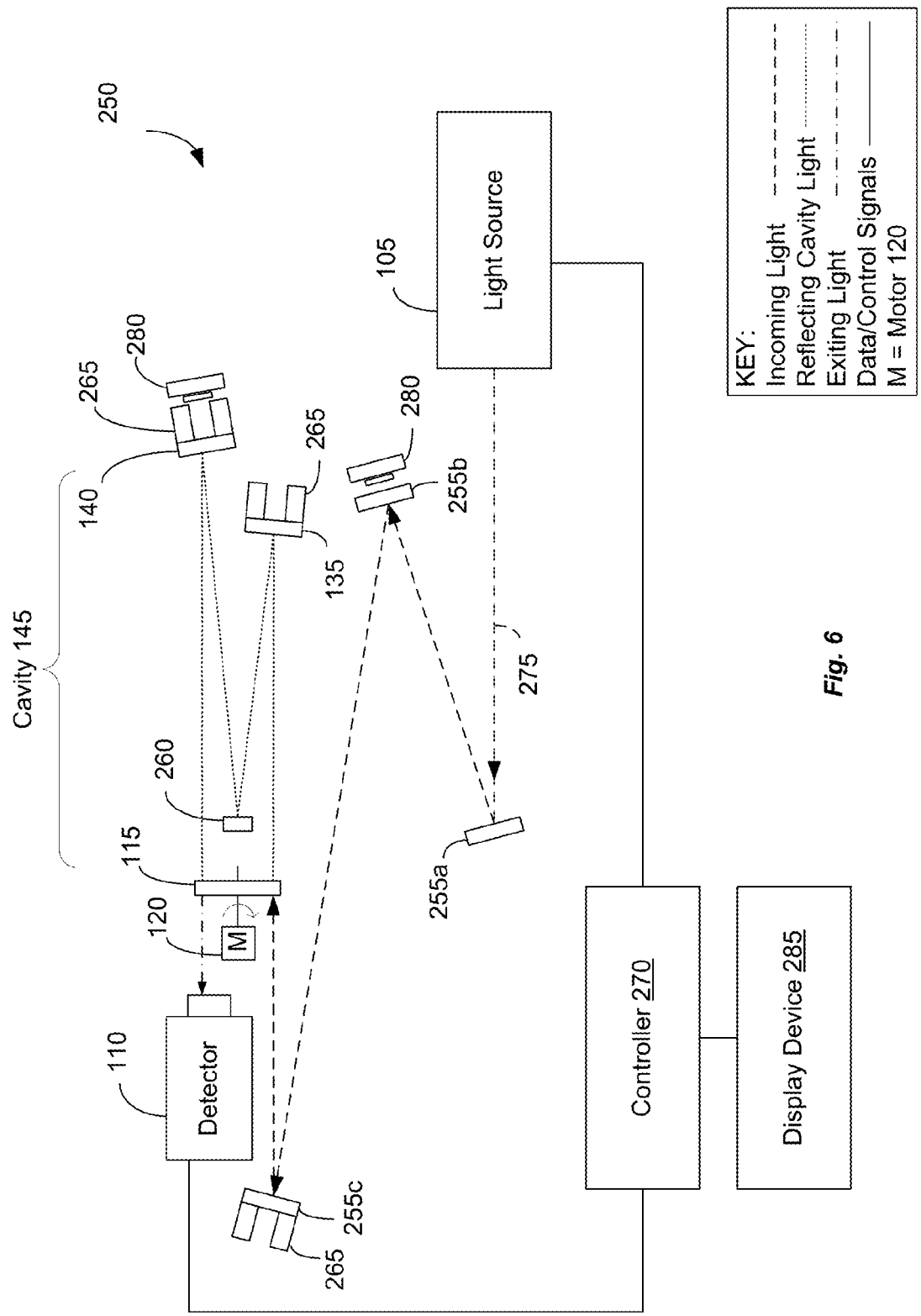
FIG. 6 illustrates in detail a variable path length spectrometer system.

FIG. 6 illustrates a spectroscopy system 250, which employs the variable path length concepts of system 100 and includes several like-numbered elements. The system 250 includes the light source 105, the detector 110, several pre-cavity mirrors 255, reflectors 135 and 145 implemented as concave folding mirrors, an additional concave folding mirror 260, and rotating reflector 115. In system 250, the reflecting arrangement 125 may be considered to include the mirror 260 in addition to the reflectors 135 and 140. During operation, the pre-cavity mirrors 255a-c, reflectors 135 and 140, and mirror 260 are generally fixed. However, pre-cavity mirror 255c, as well as reflectors 135 and 140, include actuators 265 for pre-operation alignment and for real-time alignment adjustments that occur during operation. That is, the mirror 255c and reflectors 135 and 140 are adjusted to properly reflect a beam 275 from the light source 105. The actuators 265 may be controlled manually via controller 270. Alternatively, or in addition, some mirrors may be equipped with a camera 280 to detect the beam 275, communicate with the actuators 260 (either directly or via the controller 270) to automatically align the mirrors. In some instances, the controller 270 includes alignment software for performing a feedback-controlled alignment of the mirrors based on reference signals. In some embodiments, the reflector 135, the reflector 140, the mirror 260, and the pre-cavity mirrors 255a-c each have one or more of the actuator 265 and camera 280, or have a different combination of actuators 265 and cameras 280 than shown in FIG. 6. The controller 270 is further coupled to the motor 120 to control the rotation thereof. Additionally, the controller 270 may be coupled to one or more sensors for detecting motor position, motor speed, motor acceleration, light emitted from the light source 105 (e.g., for timing purposes), rotating reflector 115 position, rotating reflector 115 velocity, and rotating reflector 115 acceleration, among other characteristics of the system 250.

The controller 270 is further coupled to a display device 285. The display device 285 receives output from the controller 270, such as results of testing, test settings, and other data for display to a user. For instance, in some embodiments, the display device is a personal computer, laptop, or tablet device. In some embodiments, the controller 270 is integrated with the display device 285. In some embodiments, the display device 285 and/or controller 270 are in communication with a remote computing device (e.g., via a local area network, wide area network, cellular network, the Internet, etc.) to enable remote set-up, testing, and review of test results.

Figure 7:
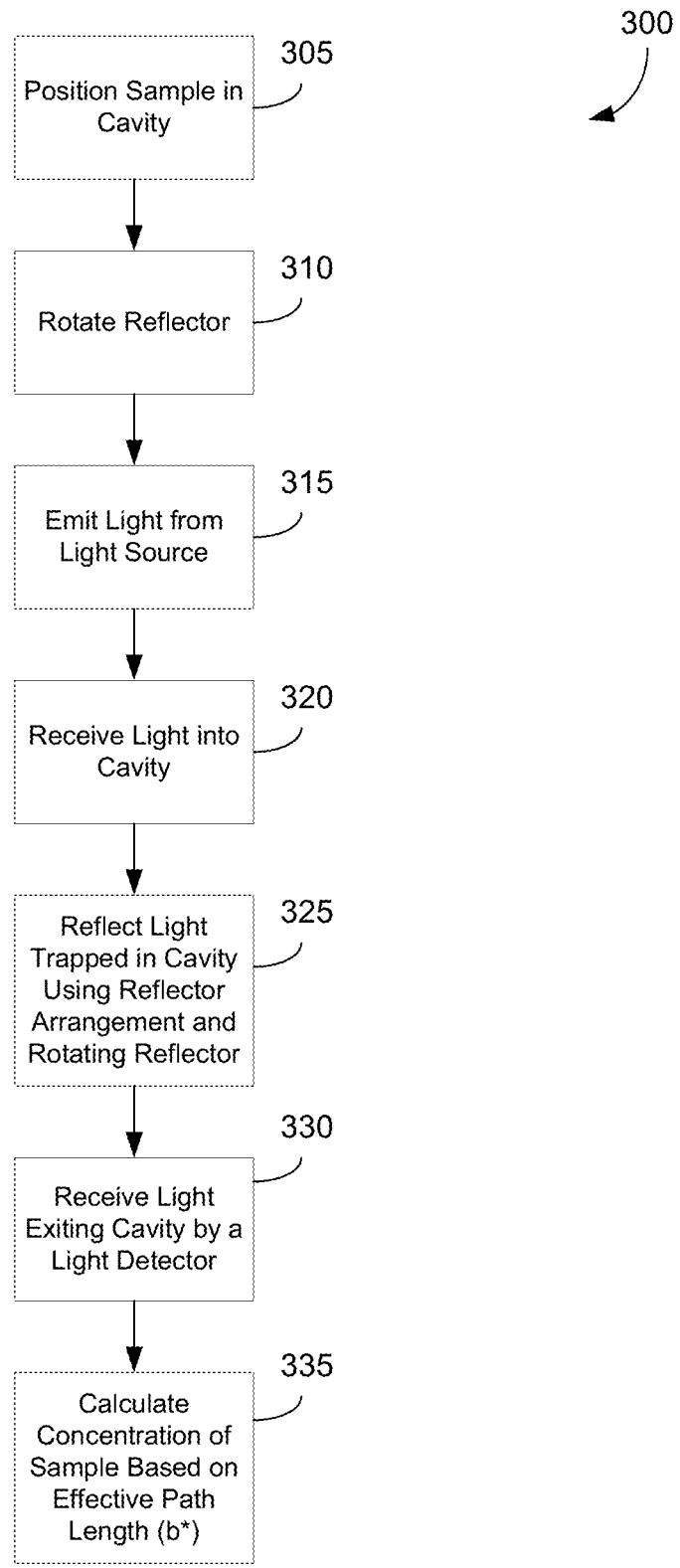
FIG. 7 illustrates a method for analyzing a sample with a variable path length spectrometer.

FIG. 7 illustrates a method 300 of operating the system 250 of FIG. 6. In step 305, a sample is positioned within the cavity 145. In step 310, the controller 270 causes rotation of the rotating reflector 115 and, in step 315, the controller 270 causes the light source 105 to emit light. The emitted light is directed by pre-cavity mirrors 255 towards the back of the rotating reflector 115. As the slit 150 rotates in front of the emitted light, the emitted light enters the cavity 145 (step 320). The rotating reflector 115 and slit 150 continue to rotate until the slit 150 is no longer in front of the emitted light (see, e.g., FIG. 2B), trapping the light within the cavity 145. In step 325, the trapped light is continuously reflected along the following path: reflector 135→mirror 260→reflector 140→rotating reflector 115→reflector 140→mirror 260→reflector 135→rotating reflector 115 (repeat) and repeatedly passes through a sample solution being analyzed (not shown, but see, e.g., FIGS. 3A-B for sample placement). The light continues to reflect until, in step 330, the slit 150 rotates to the center of the projected beam spot 200 on the rotating reflector 115, at which point the light exits the cavity 145 and is received by the detector 110. The detector 110 then outputs signals to the controller 270 indicative of the light received, which are used to determine absorption (A). The effective path length (b*) is also calculated and, along with absorption (A), the variables are used to calculate for the level of concentration (C) using Beer's Law.

FIGS. 8A-8C illustrate a system 350 having a rotating reflector 355 including multiple slits 150a-b. The system 350 includes an arrangement similar to system 100, except that the rotating reflector 355 includes two slits, slit 150a and slit 150b for providing a passage between a source side 355a and a cavity side 355b of the rotating reflector 355. The slits 150a and 150b are spaced apart by approximately 90 degrees on the surface of the rotating reflector 355. Slit 150a is an entrance slit that allows light into the cavity 145, as shown in FIG. 8A. Slit 150b is an exit slit that allows light out of the cavity 145, as shown in FIG. 8C. After entering through the slit 150a and before exiting through slit 150b, light is trapped in the cavity 145 for repeated reflection and transmission through a sample to be analyzed (see, e.g., FIG. 8B).

Figure 9A:
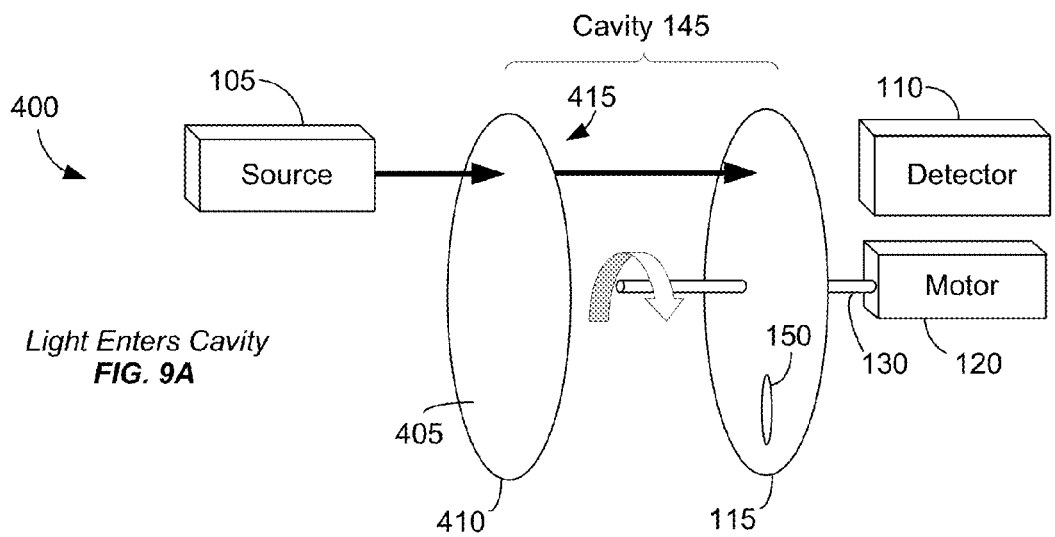
FIGS. 9A-C illustrate another variable path length spectrometer system.
Figure 9B:
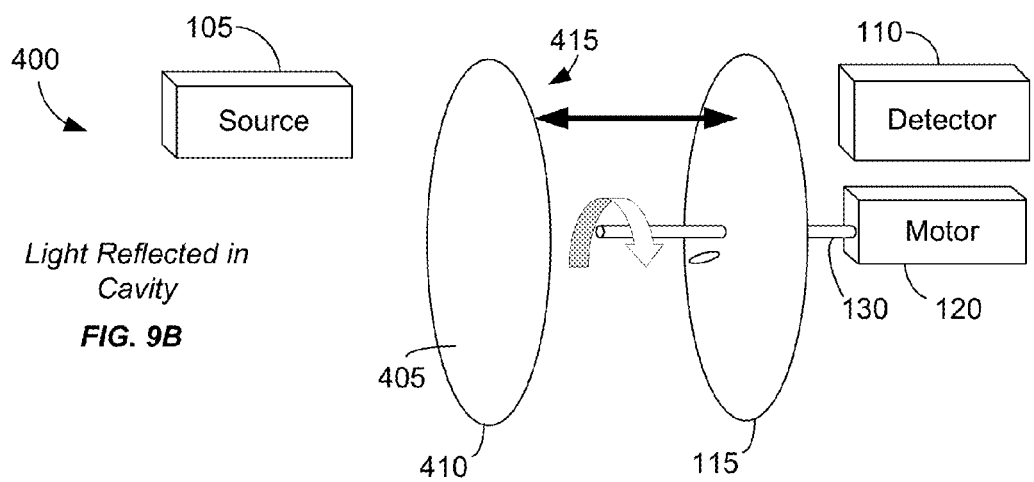
Figure 9C:
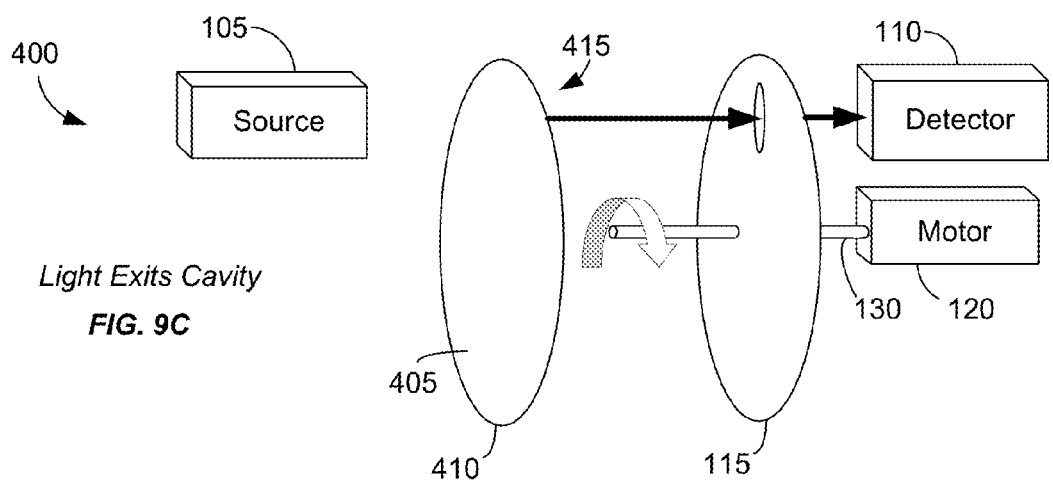

FIGS. 9A-C illustrate an alternate spectroscopy system 400. As shown in FIG. 9A, in the system 400, light is entered into the cavity 145 through a source side 405 of a fixed reflector 410, rather than through the slit 150 of the rotating reflector 115. As shown in FIG. 9B, the light within the cavity 145 is then trapped and continuously reflects between the rotating reflector 115 and the cavity side 415 of the fixed reflector 410. As shown in FIG. 9C, when the slit 150 rotates in front of the detector 110, the trapped light exits the cavity 145 and is received by the detector 110. Accordingly, the slit 150 in the system 400 is an exit slit, but not an entrance slit. As the light from the source 105 must pass through the fixed rotator 410, a portion of the light is absorbed by the fixed rotator 410, which may reduce the number of reflections possible before the light is lost due to the less-than-100% reflectivity of the fixed reflector 410 and rotating reflector 115.

Figure 10A:
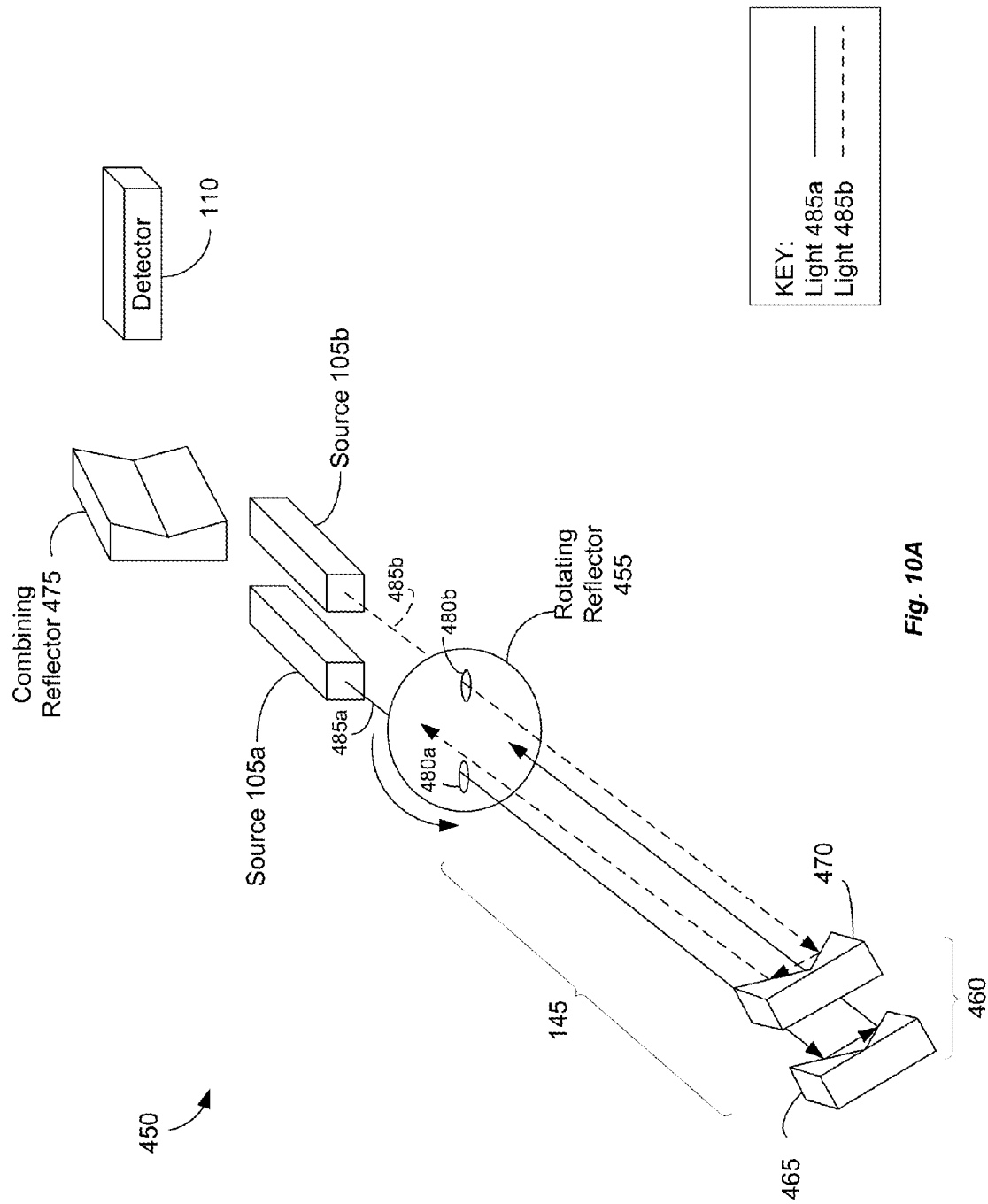
FIGS. 10A-B illustrate a dual source variable path length spectrometer system.
Figure 10B:
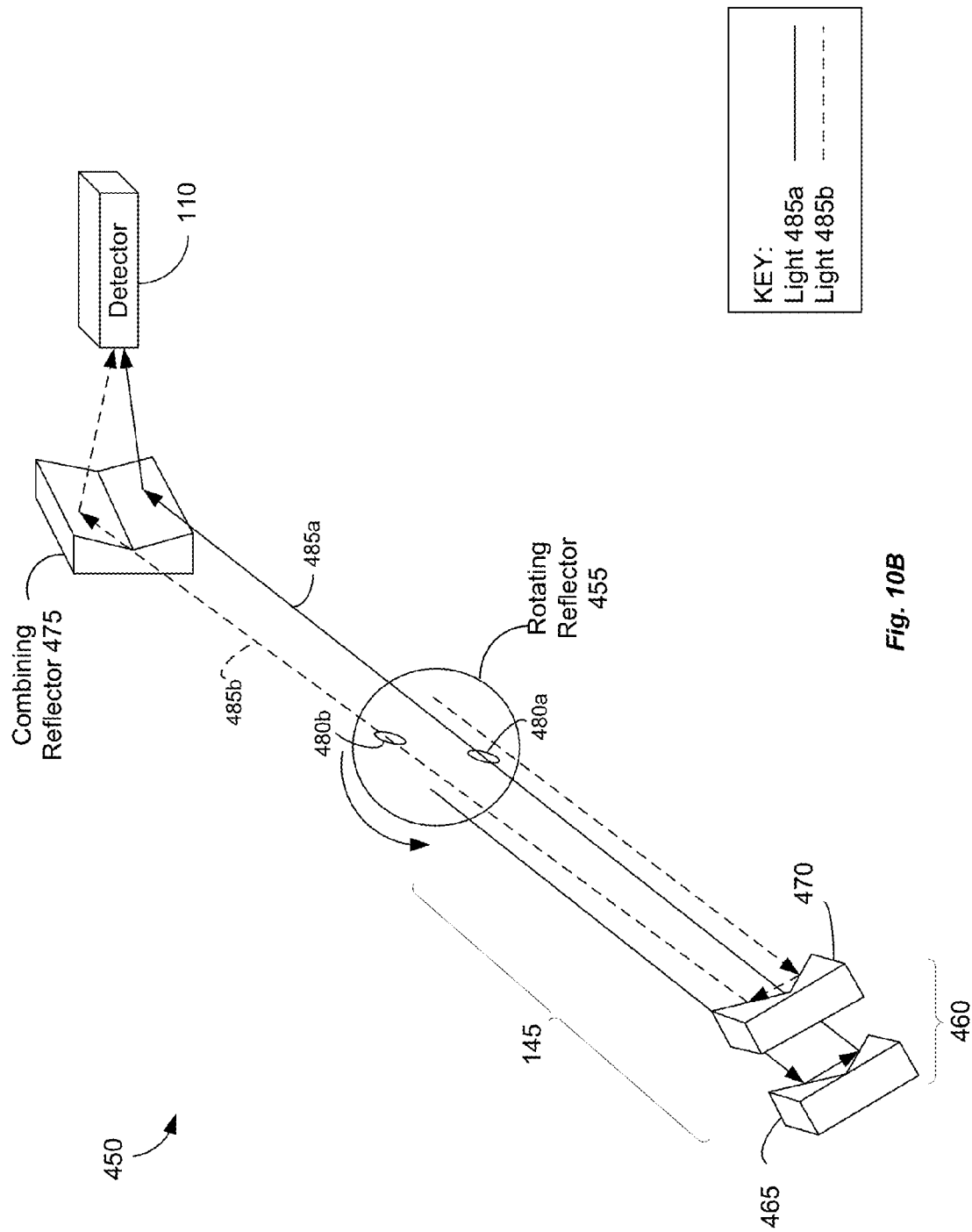

FIGS. 10A-B illustrate a dual-beam system 450. The system 450 includes two light sources 105a and 105b, each of which is similar to light source 105. The system 450 further includes a rotating reflector 455, a reflector arrangement 460 including a first reflector 465 and a second reflector 470, a combining reflector 475, and the detector 110. The rotating reflector 455 includes two slits: slit 480a and slit 480b.

In FIGS. 10A-B, the light emitted from light source 105a is depicted as solid-line light 485a, while the light emitted from light source 105b is depicted as dashed-line line 485b. The rotating reflector 455 rotates as the light 485a and light 485b are emitted from the light sources 105a and 105b. When the slits 480a and 480b rotate into the position shown in FIG. 10A, the light 485a and light 485b enter into the cavity 145 via the slits 480a and 480b, respectively. Once in the cavity 145, the light 485a is reflected off of a first face of the reflector 465 towards a second face of reflector 465, and then off of the second face of the reflector 465 back towards the rotating reflector 455. Similarly, the light 485b is reflected off of a first face of the reflector 470 towards a second face of the reflector 470, and the off of the second face of the reflector 470 back towards the rotating reflector 455.

The rotating reflector 455 continues to rotate and the slits 480a and 480b become unaligned with the light sources 105a and 105b, trapping the light 485a and 485b within the cavity 145. The light 485a and light 485b reflect between the rotating reflector 455 and the reflector arrangement 460 until the slits 480a and 480b rotate 90 degrees, as shown in FIG. 10B. In FIG. 10B, the previously trapped light 485a and light 485b exit the cavity 145 through the slits 480a and 480b, respectively. The exiting light 485a and light 485b reach the combining reflector 475. The combining reflector 475 includes two faces 475a and 475b. Face 475a is angled such that light 485a is reflected towards the detector 110. Face 475b is angled such that light 485b is reflected towards the same detector 110. Accordingly, the combining reflector 475 reflects the light 485a and light 485b to combine the signals for receipt by the detector 110. In FIG. 10B, the light sources 105a and 105b have been removed to simplify the diagram.

In general, the dual beam system 450 enables an increase in the amount of light transmitted through the sample (not shown) of the cavity 145. Additionally, the dual beam arrangement allows use of a second light source with a different wavelength for ratiometric measurements and/or for using the second beam as a reference for increased precision and accuracy. The increased light input into the cavity 145, along with the variable effective path length b* adjustable by slit position and rotation speed of the rotating reflector 455, enables the analysis of molecules having various concentration levels (C) and molar absorptivity values ($\in$) that have an absorbance level (A) that would otherwise be too small to detect (e.g., due to noise).

Figure 11A:
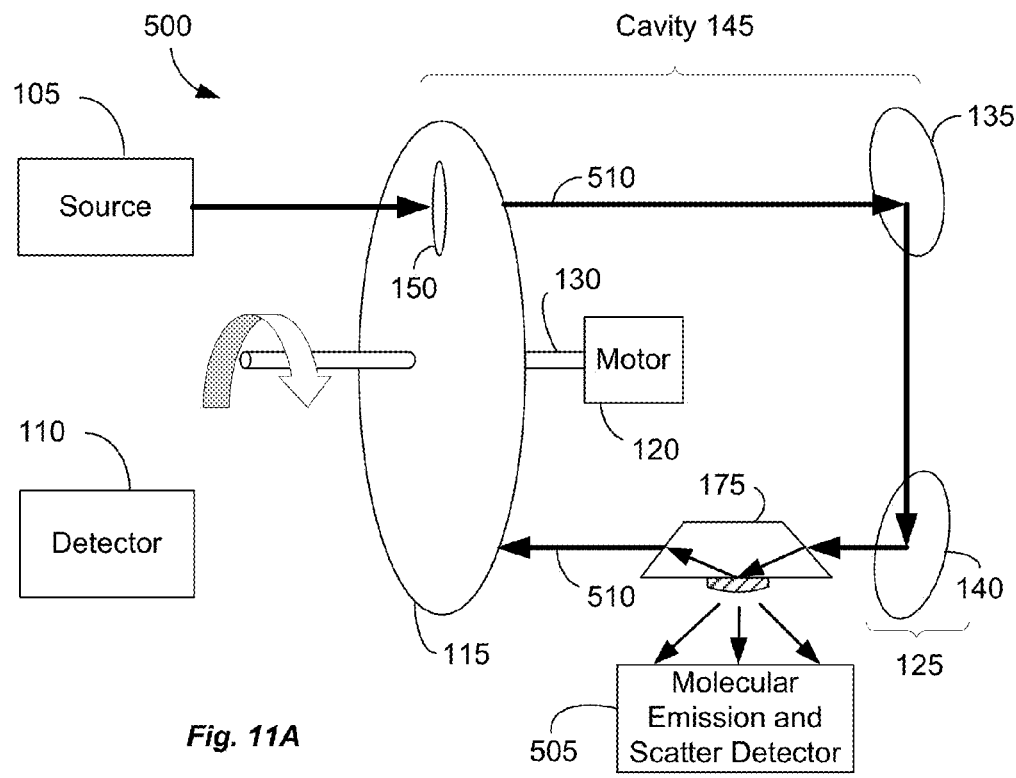
FIGS. 11A-B illustrate variable path length spectrometer systems including molecular emission and scatter detection.
Figure 11B:
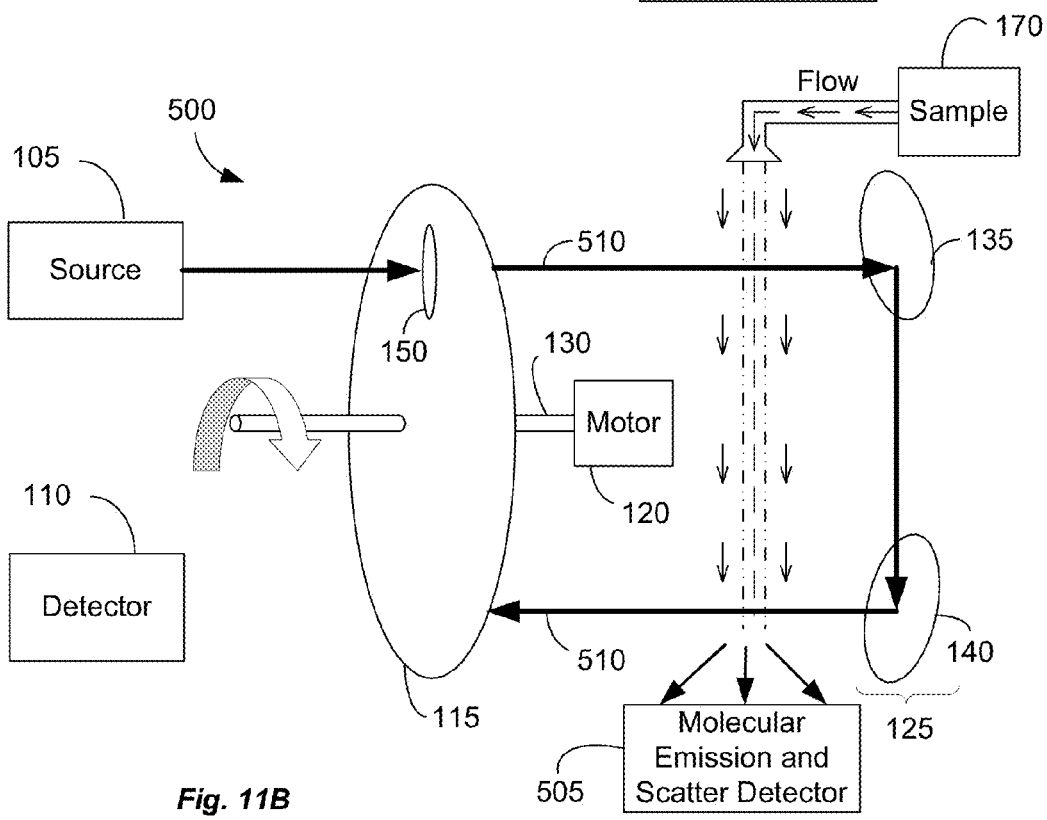

In some embodiments, the spectrometer system (e.g., system 100) described above is altered to permit light emission and scattering measurements. FIGS. 11A-B depicts such a system 500, which is system 100 including an additional emission and scatter detector 505. In FIG. 11A, the detector 505 is positioned at 90 degrees with respect to the source beam axis 510 as it passes through the sample deposited on the Dove prism 175. In FIG. 11B, the detector 505 is positioned at 90 degrees with respect to the source beam axis 510 as it passes through the flow of sample 170. In both FIGS. 11A-B, the detector 505 outputs signals to a controller (e.g., controller 270) that indicate the light received, which may be used for further analysis and calculations.

Figure 12:
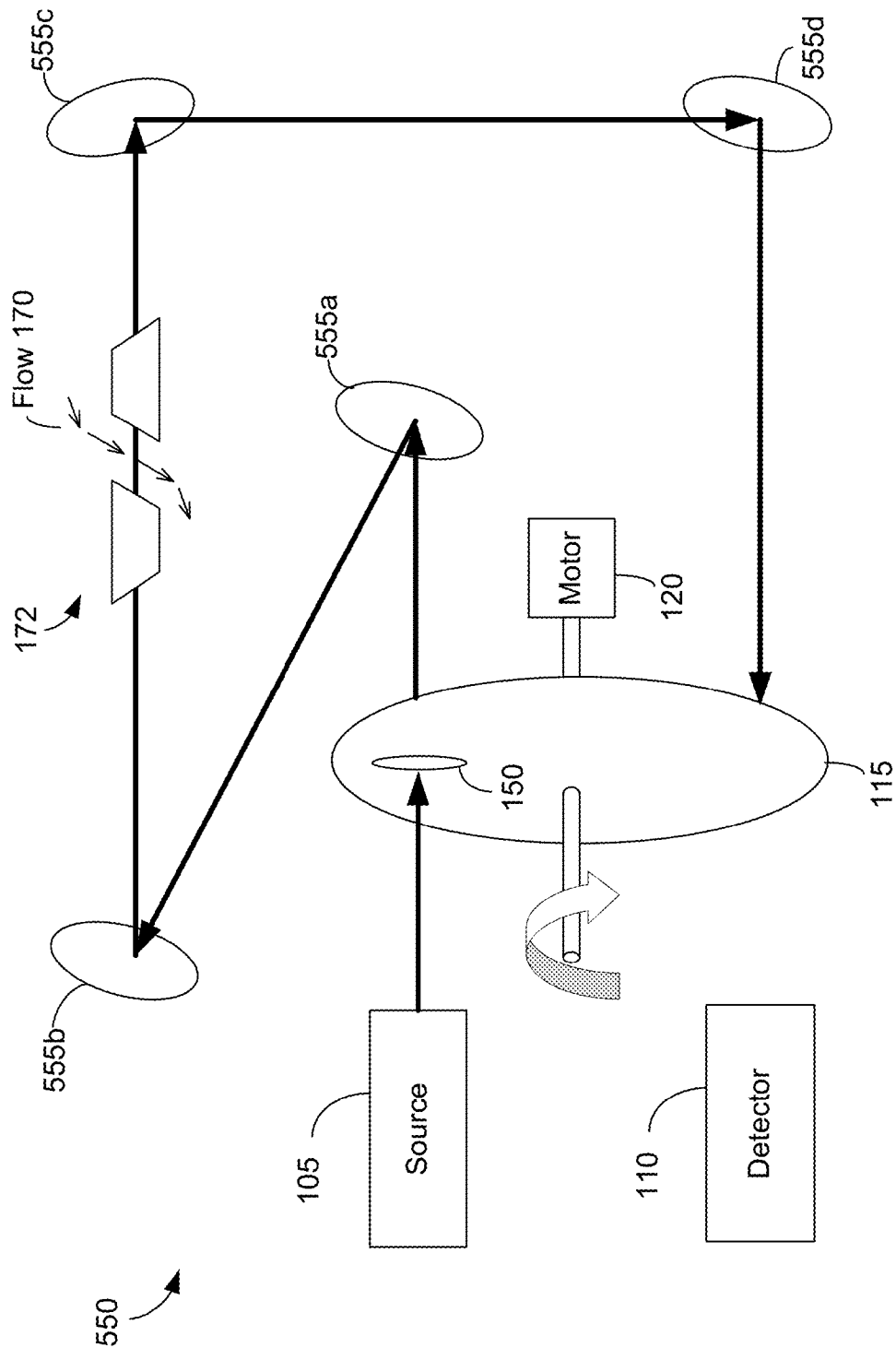
FIG. 12 illustrates another variable path length spectrometer system.

Although embodiments above illustrate the cavity 145 as being a physical space between the reflecting arrangement 125 and rotating reflector 115, the cavity 145 may be considered a reflecting cavity that is outside that particular physical space. In other words, in FIGS. 2A-C, the light reflecting within the cavity 145 is not shown to extend to the left, above, or below the rotating reflector 115, or to the right, above, or below the reflectors 135 and 140. However, turning to FIG. 12, the reflecting arrangement 555 (including reflectors 555a-d) and rotating reflector 115 form a reflecting path that reflects the light emitted from the source 105 above and to the left of the rotating reflector (see, e.g., reflector 555b). Accordingly, the term "cavity" as used in the present application is intended to describe the area in which trapped photons reflect after entrance through the slit 150 of the rotating reflector 115 and before the exit of the trapped photons through the slit 150 (or another slit) of the rotating reflector 115.

Although the slits 150, 150a-d, and 480a-b are illustrated as having a generally oval shape, other shapes may be used. For instance, the slits 150 and/or 480 may have a rectangular, circular, or other shape.

In some embodiments, the source light 105 is scanned (i.e., "rastered") horizontally across the Dove prism 175 of FIG. 4C to generate two-dimensional measurements of the sample. The detected signals may then be processed (e.g., by controller 270) to generate a two-dimensional image based on the measurements.

Embodiments of the invention disclosed above include a single rotating reflector 115 through which light enters the cavity 145 and exits the cavity 145. A prior art approach included two rotating reflectors forming a cavity for photon trapping. The two rotating reflectors included a source side reflector with an entrance slit and a detector side reflector with an exit slit. However, the two rotating reflector approach introduced additional moving parts and complexities that generally increased the difficulty of accurately reflecting the beam within the cavity and increased the potential for error. For instance, the second rotating reflector added in additional wobble to the cavity reflections, and increased the challenges associated with the precise timings involved in photon trapping spectroscopy. Accordingly, the single rotating reflector 115 provides significant advantages over the two-rotating reflector design.

Thus, the invention provides, among other things, a system and method to vary the path length (b) of light in spectroscopy, enabling the analysis of molecules having a low concentration and/or low $\in$ value. The systems and methods provide a spectroscope with a wide dynamic range (six or more orders of magnitude), low detection limits (below a part per trillion), and usable with broadband and monochromatic light sources throughout the optical region (ultraviolet to infrared). Furthermore, the effective path length (b*) is quickly adjustable via a controller, such as controller 270, altering the rotation speed of the rotating reflector. Various features and advantages of the invention are set forth in the following claims.

What is claimed is:

1. A variable path length photon trapping spectrometer comprising:
   a rotating reflector having a source side, a cavity side, and a slit providing a passage between the source side and the cavity side;
   a light source that is aligned with the slit when the rotating reflector is at a first rotational position and that emits light towards the rotating reflector and through the slit as the rotating reflector rotates;
   a cavity that receives the light that passed through the slit;
   a reflector arrangement positioned opposite the cavity side of the rotating reflector to reflect the light received by the cavity back towards the cavity side of the rotating reflector; and
   a light detector positioned opposite the source side of the rotating reflector and aligned with the slit when the rotating reflector is at a second rotational position different than the first position to receive the light reflected by the reflector arrangement, which has exited the cavity through the slit,
   wherein the light received by the cavity reflects between the reflector arrangement and the cavity side of the rotating reflector a plurality of times as the rotating reflector rotates before passing through the slit to the light detector.

2. The variable path length photon trapping spectrometer of claim 1, wherein the rotating reflector has a variable rotation speed to selectively vary a path length of the light between the light source and the light detector.

3. The variable path length photon trapping spectrometer of claim 1, wherein a sample is positioned within the cavity such that the light that passes through the slit further passes through the sample a plurality of times before exiting the cavity for receipt by the light detector.

4. A method for variable path length photon trapping spectroscopy comprising:
  rotating a rotating reflector having a source side, a cavity side, and a slit, the slit providing a passage between the source side and the cavity side;
  emitting light from a light source through the slit when the rotating reflector is at a first rotational position;
  receiving, by a cavity formed between a reflector arrangement and the rotating reflector, the light that passes though the slit;
  reflecting, by the reflector arrangement, the light back towards the cavity side of the rotating reflector; and
  receiving, by a light detector positioned opposite the source side of the rotating reflector and aligned with the slit when the rotating reflector is at a second rotational position different than the first position, the light reflected by the reflector arrangement, which has exited the cavity through the slit,
  wherein the light received by the cavity reflects between the reflector arrangement and the cavity side of the rotating reflector a plurality of times as the rotating reflector rotates before passing through the slit to the light detector.

5. The method of claim 4, further comprising varying a rotation speed of the rotating reflector to selectively vary a path length of the light between the light source and the light detector.

6. The method of claim 4, positioning a sample within the cavity such that the light that passes through the slit further passes through the sample a plurality of times before exiting the cavity for receipt by the light detector.

7. A variable path length photon trapping spectrometer comprising:
  a rotating reflector having a source side, a cavity side, a slit providing a passage between the source side and the cavity side, and a second slit;
  a light source that emits light towards the rotating reflector and through the slit as the rotating reflector rotates;
  a cavity that receives the light that passed through the slit;
  a reflector arrangement positioned opposite the cavity side of the rotating reflector to reflect the light received by the cavity back towards the cavity side of the rotating reflector; and
  a light detector positioned opposite the source side of the rotating reflector to receive the light reflected by the reflector arrangement, which has exited the cavity through the second slit,
  wherein the light received by the cavity reflects between the reflector arrangement and the cavity side of the rotating reflector a plurality of times as the rotating reflector rotates before passing through the second slit to the light detector.

8. The variable path length photon trapping spectrometer of claim 7, wherein the rotating reflector has a variable rotation speed to selectively vary a path length of the light between the light source and the light detector.

9. The variable path length photon trapping spectrometer of claim 7, wherein a sample is positioned within the cavity such that the light that passes through the slit further passes through the sample a plurality of times before exiting the cavity for receipt by the light detector.

10. A method for variable path length photon trapping spectroscopy comprising:
  rotating a rotating reflector having a source side, a cavity side, a slit providing a passage between the source side and the cavity side, and a second slit;
  emitting light from a light source through the slit;
  receiving, by a cavity formed between a reflector arrangement and the rotating reflector, the light that passes though the slit;
  reflecting, by the reflector arrangement, the light back towards the cavity side of the rotating reflector; and
  receiving, by a light detector positioned opposite the source side of the rotating reflector, the light reflected by the reflector arrangement, which has exited the cavity through the second slit,
  wherein the light received by the cavity reflects between the reflector arrangement and the cavity side of the rotating reflector a plurality of times as the rotating reflector rotates before passing through the second slit to the light detector.

11. The method of claim 10, further comprising varying a rotation speed of the rotating reflector to selectively vary a path length of the light between the light source and the light detector.

12. The method of claim 10, positioning a sample within the cavity such that the light that passes through the slit further passes through the sample a plurality of times before exiting the cavity for receipt by the light detector.

* * * * *